United States Patent [19]

Wang

[11] Patent Number: 4,885,422

[45] Date of Patent: Dec. 5, 1989

[54] CATALYTIC PROCESS FOR THE CONVERSION OF HYDROCARBONS

[75] Inventor: Li Wang, Huntington, Conn.

[73] Assignee: UOP, Des Plaines, Ill.

[21] Appl. No.: 294,843

[22] Filed: Jan. 9, 1989

Related U.S. Application Data

[62] Division of Ser. No. 99,175, Sep. 21, 1987, abandoned.

[51] Int. Cl.$^4$ .......................... C07C 2/52; C07C 12/46
[52] U.S. Cl. ...................................... 585/419; 585/418
[58] Field of Search ................................ 585/418, 419

[56] References Cited

U.S. PATENT DOCUMENTS 4,627,912 12/1986 Field .................................... 585/418
4,754,091 6/1988 Jezl et al. ............................. 585/418

Primary Examiner—Curtis R. Davis
Attorney, Agent, or Firm—Thomas K. McBride; John F. Spears, Jr.

[57] ABSTRACT

A process for converting aliphatic hydrocarbons to aromatic hydrocarbons is disclosed. The process utilizes a nonacidic hydrocarbon conversion catalyst comprising potassium form L-zeolite, a Group VIII metal, and an alumina-magnesia binder wherein the weight ratio of zeolite to binder is at least 1:1.

3 Claims, 1 Drawing Sheet

CATALYTIC PROCESS FOR THE CONVERSION OF HYDROCARBONS

CROSS-REFERENCE TO RELATED APPLICATION

This is a Divisional application of prior copending application Ser. No. 099,175 filed Sept. 21, 1987, now abandoned, the contents of which are incorporated herein by reference thereto.

BACKGROUND OF THE INVENTION

1. Field of the Invention

The present invention is directed toward a hydrocarbon-conversion process. More specifically, it relates to an improved process for the dehydrocyclization of aliphatic hydrocarbons to aromatics.

2. General Background

In the past, it has become the practice to effect conversion of aliphatic hydrocarbons to aromatics by means of the well-known catalytic reforming process. In catalytic reforming, a hydrocarbonaceous feedstock, typically a petroleum naphtha fraction, is contacted with a Group VIII-containing catalytic composite to produce a product reformate of increased aromatics content. The naphtha fraction is typically a full boiling range fraction having an initial boiling point of from about 10°–38° C. and an end boiling point of from about 107°–218° C. Such a full boiling range naphtha contains significant amounts of $C_6$-plus paraffinic hydrocarbons and $C_6$-plus naphthenic hydrocarbons.

As is well known, these paraffinic and naphthenic hydrocarbons are converted to aromatics by means of multifarious reaction mechanisms. These mechanisms include dehydrogenation, dehydrocyclization, and isomerization followed by dehydrogenation. Accordingly, naphthenic hydrocarbons are converted to aromatics by dehydrogenation. Paraffinic hydrocarbons may be converted to the desired aromatics by dehydrocyclization and may also undergo isomerization. Accordingly then, it is apparent that the number of reactions taking place in a catalytic reforming zone are numerous and the typical reforming catalyst must be capable of effecting numerous reactions to be considered usable in a commerically feasible reaction system.

Because of the complexity and number of reaction mechanisms ongoing in catalytic reforming, it has become a recent practice to develop highly specific catalysts tailored to convert only specific reaction species to aromatics. Such catalysts offer advantages over the typical reforming catalyst which must be capable of taking part in numerous reaction mechanisms. Ongoing work has been directed toward producing a catalyst for the conversion of paraffinic hydrocarbons, particularly having six carbon atoms or more, to the corresponding aromatic hydrocarbon. Such a catalyst can be expected to be much more specific resulting in less undesirable side reactions such as hydrocracking. As can be appreciated by those of ordinary skill in the art, increased production of aromatics is desirable. The increased aromatic content of gasolines as a result of lead phasedown, as well as petrochemical demand, make $C_6$–$C_8$ aromatics highly valuable products. Accordingly, it would be most advantageous to have a process ad catalytic composition which is highly selective for the conversion of less valuable $C_6$-plus paraffins to the more valuable $C_6$-plus aromatics.

To formulate catalysts capable of effecting the required reactions, it has been increasingly popular to employ crystalline aluminosilicate zeolites in combination with catalytically active metals. A well known method of preparing catalysts containing zeolites is to incorporate the zeolites into refractory inorganic matrices. Primarily, the use of such matrices, sometimes referred to as binders, has typically been directed towards simplification of catalyst manufacture, providing a simple solution to the problem associated with handling the catalytically active microparticles of zeolite. The microparticles of zeolite are combined with the binder to form or shape macroparticles which are then easily handled and utilized, for example, in a chemical reactor. Before or after forming the zeolite/binder composite, various catalytically active metals can be incorporated into the composite depending on the particular reaction to be catalyzed. Although the zeolite and the metals supply the primary catalytic effect, the contribution to the overall catalytic reaction from the binder and the particular method used to form the composite cannot be ignored. Simple changes in formulation, such as changing from 100% aulmina as the binder material to a mixture of alumina and silica, can have a dramatic effect on catalytic performance. Likewise, the use of either acidic or basic solutions during preparation of the catalyst can have an effect on the catalytic performance of the finished catalyst. Therefore, with this in mind, Broad general teachings relating to catalyst preparation do not typically lead one skilled in the art to design an effective catalyst formulation for specific applications, such as, the reforming of aliphatic hydrocarbons to aromatics.

INFORMATION DISCLOSURE

The prior art is replete with references to processes for converting aliphatic hydrocarbons to aromatic hydrocarbons and to catalysts for hydrocarbon conversion containing zeolites bound with inorganic oxide matrices. However, it is believed that none of the prior references recognizes the aromatization process of the present invention.

U.S. Pat, 4,627,912 teaches a process for contacting hydrocarbons with a reforming catalyst in the presence of a halogen, wherein the catalyst comprises L-zeolite, at least one Group VIII metal and an alkaline earth metal; an acidic or acidifiable inorganic oxide binder is preferred. The halogen imparts acidity to the catalyst, and an alumina-magnesia binder is not disclosed. In contradistinction, the present invention teaches a non-acidic L-zeolite and discloses that the basic nature of the alumina-magnesia binder results in improved selectivity to aromatics.

Other references disclose hydrocarbon conversion catalyst compositions and methods of preparation of zeolites bound with inorganic oxide matrices. For example, two similar patents, U.S. Pat. Nos. 3,945,943 and 4,120,825, teach a zeolite-refractory oxide combination that is prepared by calcining an ammonium, stabilized hydrogen-form zeolite in order to decompose the ammonium ion. U.S. Pat. No. 4,151,119 discloses a three-component catalyst comprising (1) a zeolite, (2) an inorganic oxide gel, and (3) a porous adsorbent wherein the inorganic oxide gel comprises pricipally silica with about 1 to 15% zirconia and 0.2 to 2% alumina. Both patents disclose reducing the alkali metal content of zeolite.

U.S. Pat. No. 4,556,478 is directed to a cracking catalyst composition comprising 3 to 40 wt.% zeolite and 60 to 97 wt.% alumina-magnesia matrix. This reference teaches that it is highly desirable to replace the sodium cations in the zeolite with hydrogen and rate earth elements. Further, this reference teaches away from a nonacidic zeolite by expressly stating that it is undesirable to decrease acid points on the solid acid zeolite. Also, there is no mention of a nonacidic potassium-form L-zeolite nor is there recognition that this zeolite in combination with a platinum component and an alumina-magnesia binder is useful to produce aromatics in a dehydrocyclization process.

Other relevant references include U.S. Pat. No. 4,507,396 which teaches that various zeolites, including L-zeolite, can be formed with colloidal inorganic oxide materials, such as formed silica, to produce solid inorganic bodies. The preparation method disclosed in this reference requires that the zeolite and the colloidal oxide be dispersed in a water-immiscible solvent and then titrated with an aqueous phase to produce a hydrous plastic agglomerate. U.S. Pat. N. 4,434,311 teaches that L-zeolite can be combined with an inorganic oxide to prepare catalyst particles. In particular, it is mentioned that the L-zeolite can be mixed with a colloidal suspension of silica in water, stabilized with a small amount of alkali, and extruded to form cylindrical pellets. Extrusion aids selected from ethylene glycol and stearic acid may also be employed. Similarly, U.S. Pat. No. 4,608,356 discloses a method of preparing a reforming catalyst wherein an inorganic oxide is mixed with a large-pore zeolite to form a mixture, the mixture is extruded to form an extrudate, and the extrudate is dried and calcined. None of the three just-mentioned references teach the utility of binding a nonacidic potassium-form L-zeolite in an alumina-magnesia matrix.

In summary then, the art has not recognized a process for converting aliphatic compounds to aromatic compounds utilizing a catalyst comprising a Group VIII metal component, a nonacidic L-zeolite, and an alumina-magnesia binder wherein the weight ratio of L-zeolite to alumina-magnesia binder is at least 1:1.

OBJECTS AND EMBODIMENTS

It is, therefore, a principal object of the present invention to provide a process for the conversion of aliphatic compounds to aromatic compounds. A more specific objective is to provide a process for the conversion of $C_6$-$C_8$ paraffinic hydrocarbons, to their corresponding aromatics.

Accordingly, a broad embodiment of the present invention is a process for converting aliphatic hydrocarbons to aromatic hydrocarbons comprising contacting $C_6$-$C_8$ hydrocarbons in a reaction zone at dehydrocyclization conditions with a catalyst comprising a Group VIII metal component, a nonacidic potassium form L-zeolite, and an alumina-magnesia binder wherein the weight ratio of L-zeolite to alumina-magnesia is at least 1:1.

These as well as other objects and embodiments will become evident from the following, more detailed description of the present invention.

DETAILED DESCRIPTION OF THE INVENTION

Figure 1:
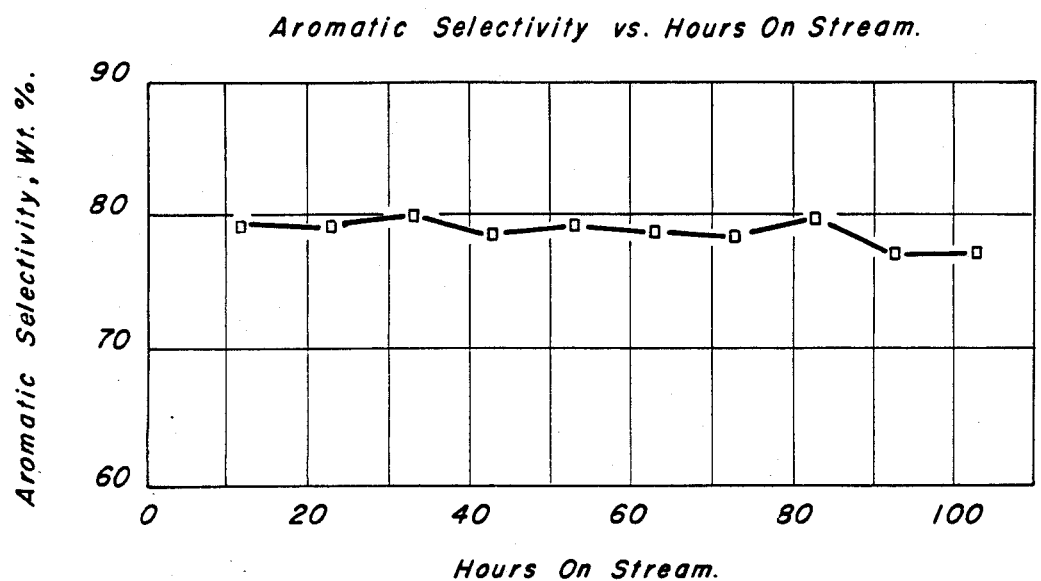
FIG. 1 is a graphical depiction of the selectivity to aromatics for the catalyst of the invention as a function of catalyst life measured in number of hours-on-stream.

To reiterate briefly, the present invention relates to a process for converting aliphatic hydrocarbons to aromatic hydrocarbons utilizing a hydrocarbon conversion catalyst which incorporates a novel combination of components. The improved basicity of the instant catalyst allows for increased selectivity to aromatics production when compared to catalysts of the prior art. Physical integrity, as measured by crushing strength, is also superior.

Accordingly, the present invention involves contacting a hydrocarbon charge stock with a novel hydrocarbon conversion catalyst at dehydrocyclization conditions. Dehydrocyclization conditions include a pressure of from about 101 to about 4137 kPa (ga), with the preferred pressure being from about 172 to about 1379 kPa (ga), a temperature of from about 350° to 650° C., and a liquid hourly space velocity of from about 0.1 to about 10 hr$^{-1}$. Preferably, hydrogen may be employed as a diluent. When present, hydrogen may be circulated at a rate of from about 0.2 to about 10 moles of hydrogen per mole of charge stock hydrocarbon.

In accordance with the present invention, a hydrocarbon charge stock is contacted with the catalyst in a hydrocarbon conversion zone. This contacting may be accomplished by using the catalyst in a fixed-bed system, a moving-bed system, a fluidized-bed system, or in a batch-type operation. The hydrocarbon charge stock and, if desired, a hydrogen-rich gas as diluent are typically preheated by any suitable heating means to the desired reaction temperature and then are passed into a conversion zone containing the catalyst of the invention. It is, of course, understood that the conversion zone may be one of more separate reactors with suitable means therebetwee to ensure that the desired conversion temperature is maintained at the entrance to each reactor. It is also important to know that the reactants may be contacted with the catalyst bed in either upward, downward, or radial-flow fashion. When the final shape of the catalyst is spherical, the latter method is preferred. In addition, the reactants may be in the liquid phase, a mixed liquid-vapor phase, or a vapor phase when they contact the catalyst. Best results are obtained when the reactants are in the vapor phase.

After contact with the catalyst, the hydrocarbon charge stock having undergone dehydrocyclization is withdrawn as an effluent stream from the reaction zone and passed through a cooling means to a separation zone. In the separation zone, the effluent may be separated into various constituents depending upon the desired products. When hydrogen is utilized as a diluent in the reaction zone, the separation zone will typically comprise a vapor-liquid equilibrium separation zone and a fractionation zone. A hydrogen-rich gas is separated from a high octane liquid product containing aromatics generated within the dehydrocyclization zone. After separation, at least a portion of the hydrogen-rich gas may be recycled back to the reaction zone as diluent. The balance of the hydrogen-rich gas may be recovered for use elsewhere. The high octane liquid product comprising aromatics may then be passed to a fractionation zone to separate aromatics from the unconverted constituents of the charge stock. Alternatively, the liquid product may be passed to either a solvent extraction process or molecular sieve separation process to accomplish the separation of aromatics from unconverted materials. These unconverted constituents may then be passed back to the reaction zone for processing or to other processes for utilization elsewhere.

A wide range of hydrocarbon charge stocks may be employed in the process of the present invention. The preferred charge stock comprises $C_6$-$C_8$ nonaromatic hydrocarbons. The exact charge stock utilized will, of course, depend on the precise use of the catalyst. Typically, hydrocarbon charge stocks which may be used in the present invention will contain naphthenes and paraffins, although in some cases, aromatics and olefins may be present. Accordingly, the class of charge stocks which may be utilized includes straight-run naphthas, natural naphthas, synthetic naphthas, and the like. Alternatively, straight-run and cracked naphthas may also be used to advantage. The naphtha charge stock may be a full-boiling range naphtha having an initial boiling point of from about 10°-70° C. and an end boiling point within the range of from about 163°-218° C., or may be a selected fraction thereof. Generally, any feed rich in paraffinic hydrocarbons will be applicable, preferably those with a low percentage of branched paraffins, such as, raffinates from aromatic extraction processes or extracts from molecular sieve separation process. These highly paraffinic feeds have an end boiling point within the range of from about 95° to 115° C. It is preferred that the charge stocks employed in the present invention be treated by conventional catalytic pretreatment methods such as hydrorefining, hydrotreating, hydrodesulfurization, etc., to remove substantially all sulfurous, nitrogenous, and water-yielding contaminants therefrom. Alternatively, feed pretreatment may be accomplished by non-hydroprocessing methods, such as, contacting with non-catalytic adsorbents, molecular sieves, activated carbons, high surface area aluminas, and high surface area sodium driers.

It is preferred that the charge stock of the instant invention substantially comprise paraffins. This, of course, is a result of the fact that the purpose of a dehydrocyclization process is to convert paraffins to aromatics. Because of the value of $C_6$-$C_8$ aromatics, it is additionally preferred that the hydrocarbon charge stock comprise $C_6$-$C_8$ paraffins. However, notwithstanding this preference, the hydrocarbon charge stock may comprise naphthenes, aromatics, and olefins in addition to $C_6$-$C_8$ paraffins.

As previously indicated, it is an essential feature of the catalyst of the present invention that it comprises a nonacidic L-zeolite. Rare earth metals, hydrogen ions and precursors to hydrogen ions, such as ammonium ions, impart acidity to zeolites and have the effect of lowering the selectivity of finished catalyst composition containing such zeolites when utilized in the process of producing aromatics from $C_6$-$C_8$ paraffinic feeds. Accordingly, it is preferred that the L-zeolite of the instant invention contain only cations that are nonacidic in nature. By "nonacidic zeolite", it is to be understood that it is meant that the zeolite has substantially all of its cationic sites of exchange occupied by nonhydrogen cationic species. Preferably, such cationic species will comprise the alkali metal cations although other cationic species may be present. Irrespective of the actual type of cationic species present in the sites of exchange, the nonacidic zeolite in the present invention has substantially all of the cationic sites occupied by nonhydrogen cations, thereby rendering the zeolite substantially fully cationic exchanged. It is most preferred that substantially all of the ion exchange sites of the L-zeolite are occupied by potassium cations. Many means are well known in the art for arriving at a substantially fully cationic exchanged zeolite and thus they need not be elaborated herein.

The especially preferred type of nonacidic zeolite of the present invention is L-zeolite. It is required that the cationic exchangeable sites of the L-zeolite be fully cationic exchanged with nonhydrogen cationic species. As also indicated above, typically the cations occupying the cationic exchangeable sites will comprise one or more of the alkali metals including lithium, sodium, potassium, rubidium, and cesium. An especially preferred nonacidic zeolite for application in the present invention is the potassium form of L-zeolite. It should also be understood, however, that thenonacidic L-zeolite of the invention may contain more than one type of the alkali metal cation at the cationic exchangeable sites, for example, lithium and potassium.

In order to allow the L-zeolite to be utilized in a convenient manner, it is necessary to combine it with a binder material. As mentioned above, utilizing a binder material allows for the formation of catalyst particles large enough in size to permit easy commercial handling, typically such particles have diameters of approximately 1/16 of an inch.. Although the art teaches that any refractory inorganic oxide binder material will be suitable, we have found that a particular inorganic oxide material, not recognized in the art in combination with nonacidic L-zeolite, when prepared in accordance with the instant invention yields a superior finished catalyst composite. In particular, the preferred binder material is alumina-magnesia.

The alumina-magnesia binder is a synthetic product or a product obtained by treating a natural clay material, which consists mainly of alumina ($Al_2O_3$) and magnesia (MgO). The alumina-magnesia of the instant invention is to be distinguished from magnesium aluminate spinel which is a crystalline material formed by high temperature calcination. For this reason, the alumina-magnesia is not exposed to calcination temperatures of greater than 800° C. The binder of the instant invention is comprised of a mixture of alumina and magnesia that is inorganic, porous, and amorphous. It is believed that the advantages obtained in utilizing alumina-magnesia in the instant invention is due to its inherent basic properties. It is this basic nature that results in improved selectivity to aromatics when compared to similar catalysts containing only alumina as the binder material.

The alumina-magnesia component can be prepared in accordance with methods known to the art. No special significance attaches to the particular method chosen. A preferred method of preparing the alumina-magnesia involves commingling a solution of aluminum nitrate with a solution of magnesium nitrate to obtain a single solution having approximately twice the weight of aluminum atoms as compared to magnesium atoms. To this solution is added a gelation-inducing compound, for example, ammonium hydroxide. It is preferred that the gelation occurs in a basic environment. It is most preferred that gelation occurs at a pH of at least 8. Gelation of the commingled aluminum and magnesium forms a hydrogel of alumina-magnesia. The hydrgol is washed with an aqueous solution and filtered to produce a filter cake. This filter cake is characterized by a high moisture content, typically containing greater than 80 wt.% volatiles. A portion of this filter cake hydrogel is dried and ground to obtain a power of alumina-magnesia. It is preferred that no more than 50 wt.%, dry basis, of the hydrogel is dried.

The nonacidic potassium form L-zeolite, hydrogel alumina-magnesia, and powdered alumina-magnesia are admixed to form an extrudable dough. An extrudable dough is one that has the correct moisture content to allow for the formation of extrudates that have acceptable integrity to withstand direct calcination. Extrudability is determined from an analysis of the moisture content of the dough. A moisture content in the range of from 30 to 50 wt.% is preferred. By incorporating hydrogel alumina-magnesia into the dough admixture, the need for extrusion aids or peptizing solutions is eliminated. The moisture content of the hydrogel supplies the necessary lubrication needed to form the extrudates. The weight ratio of L-zeolite to hydrogel alumina-magnesia and powdered alumina-magnesia can range from about 1:4 to 9:1 based on a water-free weight analysis of all the materials. A weight ratio ranging from about 1:1 to about 6:1, on a water-free basis, is most preferred. The weight ratio of hydrogel to powder is adjusted to achieve an extrudable dough at the desired level of nonacidic L-zeolite. For example, at a 70 wt.% zeolite leve, it is preferred that the weight ratio of hydrogel to powder be about 4:1.

Extrusion of the dough to form an extrudate is performed in accordance with the techniques well known in the art. A multitude of different exrudate shapes are possible, including, but not limited to, cylinders, cloverleaf, dumbbell and symmetrical and asymmetrical polylobates. It is also within the scope of this invention that the extrudates may be further shaped to any desired form, such as, spheres, by any means known to the art.

As mentioned, it is critical to the instant invention that the catalyst composite be nonacidic. Thus, it is highly desired that in no instance during the catalyst preparation will the composition be subjected to any treatment or compounds that have the effect of imparting acidity to the final composite. Preserving the potassium cations in the extrudate, as well as preserving the basicity imparted to the extrudate by the alumina-magnesia binder, are essential aspects in the preparation of the catalyst. Thus, the instant invention does not employ any steps prior to calcination, such as, washing with acid and/or ammonium solutions or replacement of the alkali cations by ion exchange techniques, which would neutralize the basicity of the extrudate. Moreover, it is a requirement of the instant invention that the extrudates are subject directly to a calcination procedure, without an intermediate drying step. This direct calcination procedure is believed to result in the encapsulation of potassium ions into the catalyst support thereby preserving the basicity. The calcination of the extrudates is performed in an oxygen-containing atmosphere at a temperature of from about 260° C. to about 650° C. for a period of about 0.5 to about 2 hours. It is most preferred that the calcination be performed at a temperature less than 800° C.

A further essential feature of the catalyst of the present invention is the presence of a platinum component. Incorporation of the platinum component may be achieved by any suitable means known in the art. A preferred method incorporates the platinum component after formation of the calcined extrudate. For example, the platinum component may be incorporated with the calcined extrudate by impregnating the extrudate with a solution of dilute chloroplatinic acid or by ion exchanging the potassium cations of the L-zeolite with a solution of tetra-amine platinum chloride. Regardless of the means chosen, it is preferred that a potassium component is included with the solution containing the platinum component. Any potassium compound or mixtures of potassium compounds that will readily dissociate in a particular solvent chosen can be utilized, such as, potassium chloride, potassium citrate, potassium acetate, potassium carbonate, potassium bicarbonate, and the like. A ion exchange procedure using a solution comprising tetra-amine platinum chloride and potassium chloride is the preferred procedure for incorporating the platinum with the catalyst. It is further preferred that the molar ratio of potassium to platinum in solution be at least about 3:1. The amount of platinum component added to the catalyst is from about 0.01 to about 5 wt.% based on the total weight of the finished catalyst, with a most preferred platinum content of from 0.5 to 2 wt.%.

Regardless of the details of how the platinum component of the catalyst is combined with the L-zeolite and alumina-magnesia binder, the final catalyst generally will be dried at a temperature of about 93° to about 316° C. for a period of from about 0.5 to about 24 hours or more, and finally oxidized at a temperature of about 316° to about 550° C. n an air atmosphere, preferably at 350° C., for a period of about 0.5 to about 10 hours. After the oxidation step, it is preferred that the catalyst be subjected to a substantially water-free reduction step prior to its use in the conversion of hydrocarbons. This step is designed to ensure a uniform and finely divided dispersion of the platinum component throughout the nonacidic potassium form L-zeolite. Preferably, substantially pure and dry hydrogen (i.e., less than 20 vol. ppm $H_2O$) is used as the reducing agent in this step. The reducing aget is contacted with the oxidized catalyst at a temperature of about 300° to about 550° C., preferably at 350° C., and for a period of time of about 0.5 to 10 hours or more, effective to reduce substantially all of the platinum component. It is preferred that the contact time in the reducing atmosphere be no longer than necessary in order to avoid any predeactivation of the catalyst which may occur. This pre-deactivation of the catalyst would show up as lower than expected activity performance when the catalyst was used in a hydrocarbon conversion process. This reduction treatment may be performed in situ as part of a startup sequence if precautions are taken to predry the plant to a substantially waterfree state and if substantially water-free hydrogen is used.

In addition to comprising a platinum component, it is contemplated in the present invention that the catalyst thereof may contain other metal components well known to have catalyst modifying properties. Such metal components include rhenium, iridium, tin, cobalt, indium, gallium, lead, zinc, uranium, thallium, dysprosium, germanium, etc. Incorporation of such metal components have proven beneficial in catalytic reforming as promoters and/or extenders. Accordingly, it is within the scope of the present invention that catalytically effective amounts of such modifiers may be beneficially incorporated into the catalyst of the present invention improving its performance.

In order to more fully demonstrate the attendant advantages arising from the present invention, the following examples are set forth. It is to be understood that the following is by way of example only and is not intended as an undue limitation on the otherwise broad scope of the present invention.

It should be understood that there are three parameters especially useful in evaluating and comparing dehydrocyclization catalysts. The first is "activity" which is a measure of the catalyst's ability to convert reactants at a specified set of reaction conditions. The second catalyst performance criteria is "selectivity" which is an indication of the catalyst's ability to produce a high yield of the desired product. The third parameter is "stability" which is a measure of the catalyst's ability to maintain its activity and selectivity over time. In the appended examples, the criteria which will be of interest is catalyst selectivity. Selectivity is defined as the quotient of the yield of a particular species foud in the product divided by the percent conversion of feed material. For purposes of the example, the measure of catalyst selectivity is the production of aromatics. Also indicative of a highly selective catalyst is a low production of light hydrocarbons, namely, $C_1$ to $C_4$ hydrocarbons.

EXAMPLE

A first solution of aluminum nitrate and magnesium nitrate was prepared wherein the weight ratio of aluminum atoms to magnesium atoms is about 2:1. To this first solution was added a second solution of $NH_4OH$. The second solution was added slowly maintaining the pH of the first solution at 8 until gelation of the aluminum and magnesium occurred. The hydrogel of alumina-magnesia was slurried with water and filtered to obtain a filter cake having a moisture content of approximately 90 wt.%. A portion of this filter cake was dried at 150° C. to a moisture content of about 60 wt.%. This dried material was then ground to produce powdered alumina-magnesia.

An extrudable dough was prepared by combining and mixing 70 wt.% nonacid potassium form L-zeolite, 24 wt.% hydrogel alumina-magnesia, and 6 wt.% powdered alumina-magnesia. The dough was then extruded through a 1/14-inch die to form cylindrical extrudates. These extrudates were directly subjected to a calcination procedure without any prior washing or drying treatments. Calcination of the extrudates occurred in flowing air for a period of 40 minutes at a temperature of 605° C.

The calcined extrudates were then subjected to an impregnation procedure using a solution of tetra-amine platinum chloride and potassium chloride. The molar ratio of potassium to platinum was about 3:1. Upon completion of the impregnation, the catalyst was dried, oxidized, and reduced to yield a catalyst containing about 1.0 wt.% platinum and 10.0 wt.% potassium oxide.

The catalyst was subjected to a test to measure its performance as a dehydrocyclization catalyst, specifically measuring the selectivity to aromatics production. The results of the tests are set forth in FIGS. 1 and 2.

The charge stock utilized in the test of this example had the following analysis:

| | |
|---|---|
| $C_6$ paraffins | 29.6 wt. % |
| $C_7$ paraffins | 32.8 wt. % |
| $C_8$ paraffins | 31.5 wt. % |
| 2 methylpentane + CP | 0.1 wt.% |
| 3 methylpentane | 0.7 wt. % |
| Methylcyclopentane | 4.1 wt. % |
| Unknown $C_7^+$ | 1.2 wt. % |

The test was run in a pilot plant having a reactor in which the catalyst to be tested was emplaced. The reactor effluent was analyzed by means of standard gas chromatograph techniques.

The conditions employed during testing of the catalysts were a 4.0 $hr^{-1}$ liquid hourly space velocity and a reaction zone pressure of 621 kPa (ga). Reaction temperature was constant. Hydrogen was admixed with the charge stock prior to contact with the catalysts. Sufficient hydrogen was used to provide a 5:1 ratio of moles of hydrogen to moles of hydrocarbon charge stock.

Figure 2:
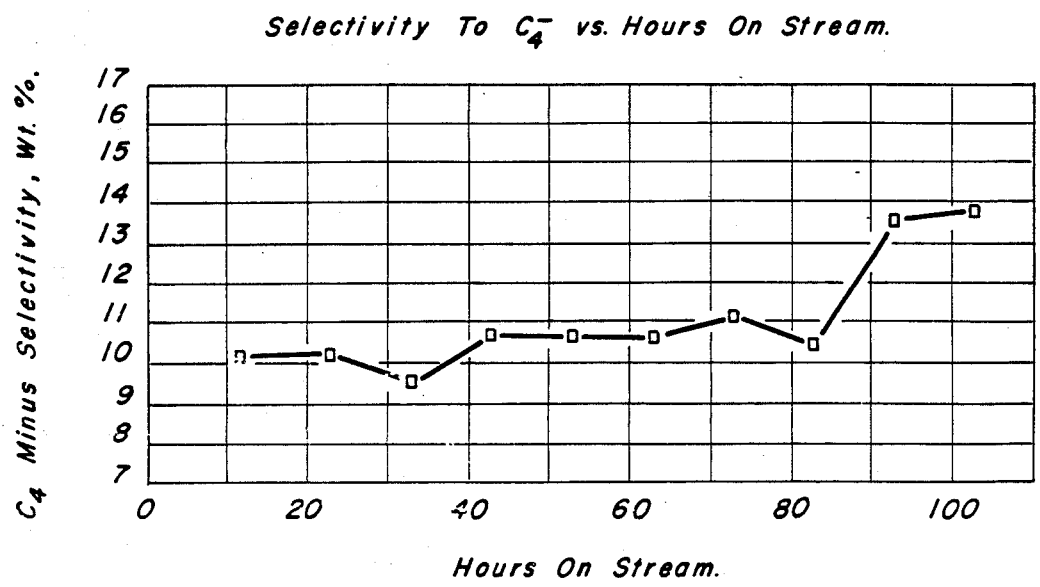
FIG. 2 is a graphical depiction of the selectivity to $C_4$-minus byproducts for the catalyst of the invention as a function of catalyst life measured in number of hours on-stream.

Results from the test run are set forth in FIGS. 1 and 2. FIG. 1 graphically illustrates the high selectivity to aromatics of the catalyst of the instant invention averaging about 79 wt.% throughout the run. FIG. 2 shows the nonacidic nature of catalyst which is evidenced by the low selectivity to light hydrocarbon by-products.

What is claimed is:

1. A process for converting aliphatic hydrocarbons to aromatic hydrocarbons comprising contacting $C_6$–$C_8$ hydrocarbons in a reaction zone at dehydrocyclization conditions with a catalyst comprising a Group VIII metal component, a nonacidic L-zeolite, and an alumina-magnesia binder wherein the weight ratio of L-zeolite to alumina-magnesia is at least 1:1.

2. The process of claim 1 further characterized in that the $C_6$–$C_8$ hydrocarbons are substantially paraffinic.

3. The process of claim 1 further characterized in that the dehydrocyclization conditions comprise a temperature of from about 350° to about 650° C., a reaction pressure of from about 101 to about 4137 kPa (ga), a liquid hourly space velocity of from 0.1 about 10 $hr^{-1}$, and a hydrogen to $C_6$–$C_8$ hydrocarbon feed mole ratio from about 0.2 to about 10.

* * * * *